US008287810B2

(12) United States Patent
Alocilja et al.

(10) Patent No.: US 8,287,810 B2
(45) Date of Patent: Oct. 16, 2012

(54) ELECTRICALLY-ACTIVE FERROMAGNETIC PARTICLE CONDUCTIMETRIC BIOSENSOR TEST KIT

(75) Inventors: Evangelyn C. Alocilja, East Lansing, MI (US); Sudeshna Pal, Okemos, MI (US); Emma B. Setterington, DeWitt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 815 days.

(21) Appl. No.: 12/214,362

(22) Filed: Jun. 18, 2008

(65) Prior Publication Data
US 2008/0314766 A1 Dec. 25, 2008

Related U.S. Application Data

(60) Provisional application No. 60/936,424, filed on Jun. 20, 2007.

(51) Int. Cl.
| G01N 27/00 | (2006.01) |
| G01N 21/75 | (2006.01) |
| G01N 31/22 | (2006.01) |
| G01N 33/52 | (2006.01) |
| G01N 25/18 | (2006.01) |
| G01N 1/00 | (2006.01) |
| G01N 1/18 | (2006.01) |
| B01L 3/00 | (2006.01) |
| C12M 1/34 | (2006.01) |
| C12M 3/00 | (2006.01) |

(52) U.S. Cl. ...... 422/82.02; 422/400; 422/420; 422/430; 422/82.01; 436/149; 436/174; 436/178; 436/808; 435/287.2; 435/287.7

(58) Field of Classification Search ............ 436/65, 436/510, 513, 514, 532, 806, 808, 809; D24/216, D24/223; 422/58, 61, 82.01, 82.02
See application file for complete search history.

(56) References Cited

U.S. PATENT DOCUMENTS

| 4,486,530 A | 12/1984 | David et al. |
| 4,786,589 A | 11/1988 | Rounds et al. |
| 4,939,096 A | 7/1990 | Tonelli |
| 4,965,187 A | 10/1990 | Tonelli |
| 5,166,078 A | 11/1992 | McMahon et al. |
| 5,169,789 A | 12/1992 | Bernstein et al. |
| 5,177,014 A | 1/1993 | O'Connor et al. |
| 5,219,725 A | 6/1993 | O'Connor et al. |
| 5,256,372 A | 10/1993 | Brooks et al. |
| 5,312,762 A * | 5/1994 | Guiseppi-Elie ............ 205/778 |

(Continued)

OTHER PUBLICATIONS

N.L. Rosi, et al. Nanostructures in Biodiagnostics. Chemical Reviews (Apr. 2005); 105(4): 1547-1562. See p. 1555, col. 2, first paragraph of section 2.2.1.*

(Continued)

*Primary Examiner* — Jill Warden
*Assistant Examiner* — Charles Hammond
(74) *Attorney, Agent, or Firm* — Dickinson Wright PLLC

(57) ABSTRACT

A membrane strip biosensor device using a fluid mobile conductive composition of ferromagnetic particles bound to a conductive polymer bound to a capture reagent is described. The biosensor device is designed to detect analytes at low concentrations in near real-time with an electronic data collection system and can be small. The device can be used to detect pathogens, proteins, and other biological materials of interest in food, water, and environmental samples.

27 Claims, 12 Drawing Sheets
(1 of 12 Drawing Sheet(s) Filed in Color)

U.S. PATENT DOCUMENTS

| | | | |
|---|---|---|---|
| 5,356,785 | A | 10/1994 | McMahon et al. |
| 5,491,097 | A * | 2/1996 | Ribi et al. ............ 436/518 |
| 5,518,892 | A | 5/1996 | Naqui et al. |
| 5,536,644 | A | 7/1996 | Ullman et al. |
| 5,559,041 | A | 9/1996 | Kang et al. |
| 5,620,845 | A | 4/1997 | Gould et al. |
| 5,620,895 | A | 4/1997 | Naqui et al. |
| 5,627,026 | A | 5/1997 | O'Connor et al. |
| 5,656,448 | A | 8/1997 | Kang et al. |
| 5,670,031 | A | 9/1997 | Hintsche et al. |
| 5,695,928 | A | 12/1997 | Stewart et al. |
| 5,700,655 | A | 12/1997 | Croteau et al. |
| 5,726,010 | A | 3/1998 | Clark |
| 5,726,013 | A | 3/1998 | Clark |
| 5,728,587 | A | 3/1998 | Kang et al. |
| 5,750,333 | A | 5/1998 | Clark |
| 5,753,456 | A | 5/1998 | Naqui et al. |
| 5,976,896 | A | 11/1999 | Kumar et al. |
| 5,985,594 | A | 11/1999 | Croteau et al. |
| 6,136,554 | A | 10/2000 | Bochner |
| 6,315,926 | B1 | 11/2001 | Jansen |
| 6,331,356 | B1 | 12/2001 | Angelopoulos |
| 6,333,145 | B1 | 12/2001 | Cloots |
| 6,333,425 | B1 | 12/2001 | Michot |
| 6,478,938 | B1 * | 11/2002 | Paek et al. ............ 204/403.01 |
| 7,541,004 | B2 * | 6/2009 | Niksa et al. ............ 422/82.02 |
| 2003/0153094 | A1 * | 8/2003 | Alocilja et al. ............ 436/516 |
| 2003/0170613 | A1 | 9/2003 | Straus |
| 2003/0178309 | A1 * | 9/2003 | Huang et al. ............ 204/547 |
| 2005/0009002 | A1 | 1/2005 | Chen et al. |
| 2007/0020700 | A1 * | 1/2007 | Carpenter et al. ............ 435/7.5 |
| 2008/0305963 | A1 * | 12/2008 | Alocilja et al. ............ 506/9 |

OTHER PUBLICATIONS

S.-J. Park, et al. Array-Based Electrical Detection of DNA with Nanoparticle Probes. Science (Feb. 22, 2002); 295(5559):1503-1506. See p. 1503, col. 2, last paragraph, running onto p. 1504; p. 1504, col. 1, first full paragraph.*

S. Dubus, et al. PCR-Free DNA Detection Using a Magnetic Bead-Supported Polymeric Transducer and Microelectromagnetic Traps. Analytical Chemistry (Jul. 1, 2006); 78(13): 4457-4464. See p. 4458, col. 1, first full paragraph; p. 4460, col. 2, first full paragraph.*

G. Farace, et al. Reagentless Biosensing Using Electrochemical Impedance Spectroscopy. Bioelectrochemistry (Jan. 2002); 55(1-2): 1-3. This entire brief paper makes the point.*

K.Y. Chumbimuni-Torres, et al. Solid Contact Potentiometric Sensors for Trace Level Measurements. Analytical Chemistry (Feb. 15, 2006); 78(4): 1318-1322. See especially p. 1319, col. 2, first two paragraphs.*

P. Poddar, et al. Magnetic Properties of Conducting Polymer Doped with Manganese-Zinc Ferrite Nanoparticles. Nanotechnology (Oct. 2004); 15(10): S570-S574. See p. S571, col. 1, first full paragraph.*

J.-H. Kim, et al. Conductimetric Membrane Strip Immunosensor with Polyaniline-Bound Gold Colloids as Signal Generator. Biosensors and Bioelectronics (Feb. 2000); 14(12): 907-915. See abstract.*

J.-H. Kim, et al. Conductimetric Membrane Strip Immunosensor with Polyaniline-Bound Gold Colloids as Signal Generator. Biosensors and Bioelectronics (Feb. 2000); 14(12): 907-915. See especially p. 908, col. 2, first paragraph of section 2.3; p. 909, col. 2, first paragraph of section 2.7; p. 913, col. 2, second full paragraph; Figs. 1, 3, 4.*

W. Luo, et al. s-Electron Ferromagnetism in Gold and Silver Nanoclusters. Nano Letters (Oct. 2007); 7(10): 3134-3137. See abstract.*

Kim et al., Biosensor & Bioelectrics 14 907, 915 (published in Feb. 2000).

Sharma R; Lamba S; Annapoorni S; Sharma P; Inoue A; (2005), Composition dependant magnetic properties of iron-oxide polyaniline nanoclusters. Journal of Applied Physics, 97 (1), 14311-14316.

Zhu N; Chang Z; He P; Fang Y; (2006). Electrochemically fabricated polyaniline nanowire-modified electrode for voltammetric detection of DNA hybridization. Electrochimica Acta, 51, 3758-3762.

Muhammad-Tahir Z; Alocilja E C (2003b), Fabrication of a disposable biosensor for *Escherechia coli* 0157:H7 detection. IEEE Sensor Journal, 3(4), 345-351.

Pal, S., Alocilja, E.C., Downes, F.P., Biosensors & Bioelectronics, 2007, 22, 2329-2336.

Stejskal J., "Polyaniline. Preparation of a Conducting Polymer," Pure Appln. Chem., vol. 74, No. 5, pp. 857-867 (2002).

* cited by examiner

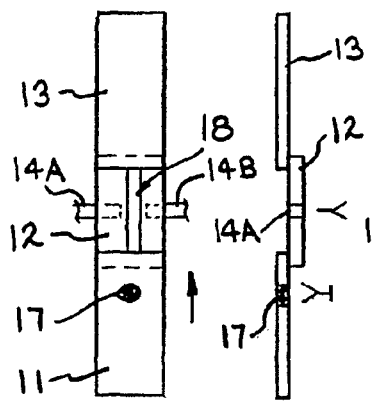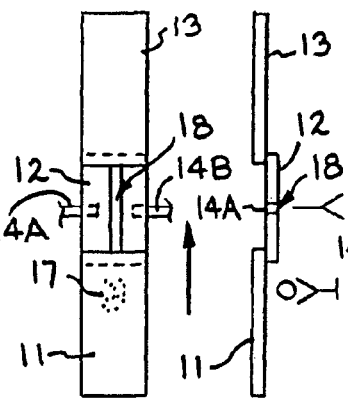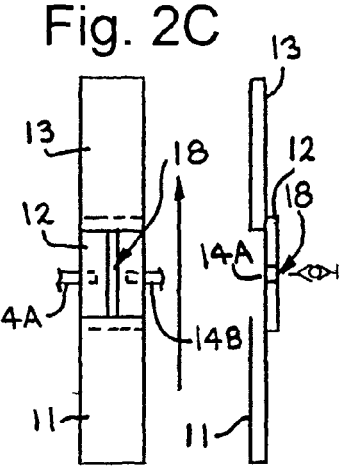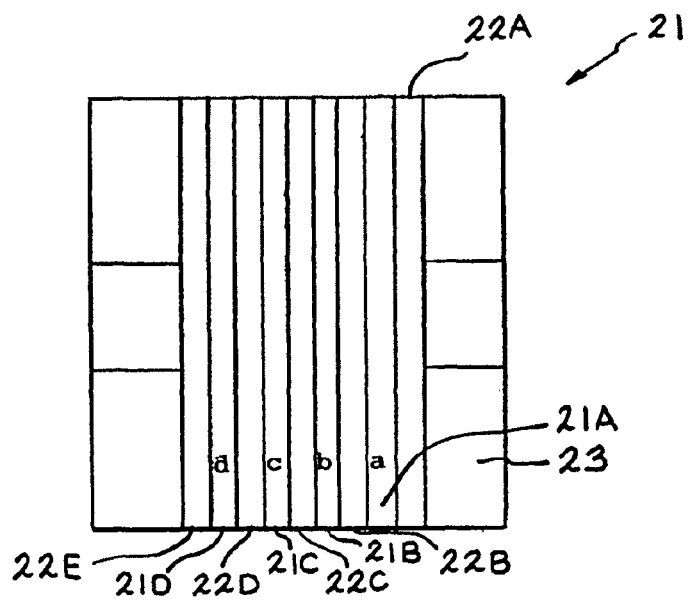

ELECTRICALLY-ACTIVE FERROMAGNETIC PARTICLE CONDUCTIMETRIC BIOSENSOR TEST KIT

CROSS-REFERENCE TO RELATED APPLICATION

This application claims benefit to U.S. Provisional Application Ser. No. 60/936,424, filed Jun. 20, 2007, which is incorporated herein by reference in its entirety.

STATEMENT REGARDING FEDERALLY SPONSORED RESEARCH OR DEVELOPMENT

Not applicable.

REFERENCE TO A "COMPUTER LISTING APPENDIX SUBMITTED ON A COMPACT DISC"

Not applicable.

BACKGROUND OF THE INVENTION (1) Field of the Invention

The present invention relates to a conductimetric biosensor device with spaced apart electrodes as part of a test kit, wherein conductance or resistance is measured between electrodes. In particular, the present invention relates to the biosensor device which uses a fluid mobile ferromagnetic particles bound to a conductive polymer bound to (moiety of) a capture reagent (such as an antibody) as a composition which captures an analyte in a fluid sample. The complex then migrates to a capture zone where the complexed analyte is captured by another capture reagent (such as a monoclonal or polyclonal antibody) bound to (immobilized on) a substrate. The conductance or resistance between the electrodes are then measured. Bacteria are particularly detected by the biosensor device. Multiple detections can be accomplished simultaneously in different parallel arrays on the biosensor device with different capture reagents and complexes between different sets of electrodes.

(2) Description of Related Art

Assays based upon conductivity or resistance are well known. Illustrative patents are U.S. Pat. No. 5,312,762 to Guiseppi-Elie and U.S. Pat. No. 5,670,031 to Hintsche et al. Illustrative published art is Kim et al., Biosensor & Bioelectrics 14 907, 915 (published in February of 2000). In this art, conductive polymers are used as sensors of analytes ('762 patent and Kim et al) and microsized test devices (Hirtsche et al) are used to detect an analyte. In Kim et al, a conductive polymer is bonded to conductive gold particles, which also serve as a visually detectable reagent, for a conductimetric assay. In this assay, the analyte in a sample is added to the test device, bound by the gold labeled particles and then targeted to a site when there is a capture reagent between electrodes. The conductimetric test is then performed. One problem with the Kim et al assay is that the sample is applied to the test device and migrates along the test device to complex with the capture reagent. The sample can contain materials which reduce the efficiency of the assay.

Various types of immunoassays based upon detecting a signal from a capture reagent are described in U.S. Pat. No. 5,620,845 to Gould et al.; U.S. Pat. No. 4,486,530 to David et al.; U.S. Pat. No. 5,559,041 to Kang et al.; U.S. Pat. No. 5,656,448 to Kang et al.; U.S. Pat. No. 5,728,587 to Kang et al.; U.S. Pat. No. 5,695,928 to Stewart et al.; U.S. Pat. No. 5,169,789 to Bernstein et al.; U.S. Pat. Nos. 5,177,014, 5,219,725, and 5,627,026 to O'Conner et al.; U.S. Pat. No. 5,976,896 to Kumar et al.; U.S. Pat. Nos. 4,939,096 and 4,965,187 to Tonelli; U.S. Pat. No. 5,256,372 to Brooks et al.; U.S. Pat. Nos. 5,166,078 and 5,356,785 to McMahon et al.; U.S. Pat. Nos. 5,726,010, 5,726,013, and 5,750,333 to Clark; U.S. Pat. Nos. 5,518,892, 5,753,456, and 5,620,895 to Naqui et al.; U.S. Pat. Nos. 5,700,655 and 5,985,594 to Croteau et al.; and U.S. Pat. No. 4,786,589 to Rounds et al. The aforementioned U.S. patents are hereby incorporated herein by reference.

OBJECTS OF THE INVENTION

It is an object of the present invention to provide a device in a test kit, a method of use and a system which enables the conductimetric (resistance or conductivity) detection of an analyte in a fluid sample using a composition which is ferromagnetic particles bound to a conductive polymer bound to a capture reagent bound to a capture reagent for the analyte. In particular, it is an object of the present invention to provide a biosensor device in a test kit for use in the method and system which reliably detects the analyte by electrical conduction or resistance between electrodes. Further, it is an object of the present invention to provide a device which can easily be miniaturized and which can be produced economically. These and other objects will become increasingly apparent by reference to the following description and the drawings.

SUMMARY OF THE INVENTION

The present invention provides a test kit which comprises: (a) a composition which is ferromagnetic particles bound to a conductive polymer bound to capture reagent for an analyte; and (b) a biosensor device for detecting the analyte which comprises: a strip of a substrate having at least two zones wherein a (1) first of the zones comprises a first capture reagent or the analyte bound to or as a moiety of the substrate in a defined area and spaced apart electrodes defining sides of the defined area for providing an electrical bias to the defined area; and (2) a second of the zones comprising a fluid transfer medium for supplying a fluid to the first zone, wherein when there is a fluid sample comprising the analyte in a complex with the composition which is the ferromagnetic particle bound to the conductive polymer bound to the capture reagent bound to the analyte, provided in the second of the zones, wherein in use the complex migrates to the first zone in the medium and the analyte and is bound by the first capture reagent thereby altering a conductivity or resistance of the defined area in the first zone as measured between the electrodes to detect the analyte. In further embodiments, the composition which is the ferromagnetic particles bound to the conductive polymer bound to the capture reagent is provided in a separate container in the test kit. In further still embodiments, the composition which is the ferromagnetic particles bound to the conductive polymer bound to the capture reagent is placed in the second zone of the biosensor device so that the analyte can bind to the composition in the second zone. In still further embodiments, the device further comprises a third zone adjacent to the first zone into which the fluid is absorbed after passing through the first defined area of the first zone. In further still embodiments, the first defined area has a dimension between the electrodes of 1.0 mm or less.

The present invention further still provides a method for detecting an analyte in a fluid sample which comprises: (a) providing a biosensor device which comprises: a strip of a substrate having at least two zones wherein a (a) first of the zones comprises a first capture reagent for the analyte bound to or as a moiety of the substrate in a defined area and spaced apart electrodes defining sides of the defined area for providing an electrical bias to the defined area; and (2) a second of the zones comprising a fluid transfer medium for supplying a fluid to the first zone, wherein when there is a fluid sample comprising an analyte bound by a second capture reagent is provided in the second zone, the complex migrates to the first zone in the fluid transfer medium and the analyte is bound by the first capture reagent thereby altering a conductivity or resistance of the defined area in the first zone as measured between the electrodes; (b) providing a fluid comprising the complex, which is the capture reagent composition, which is ferromagnetic particles bound to a conductive polymer bound to a capture reagent bound to the analyte in the second zone in the transfer medium; (c) measuring how the conductivity, resistance or magnetic properties of the first defined area is altered due to the presence of the conductive polymer bound are ferromagnetic particles to detect the analyte. In further embodiments, the composition which is the ferromagnetic particles bound to the conductive polymer bound to the capture reagent are provided in a container in a test kit. In further still embodiments, the composition which is ferromagnetic particles bound to the conductive polymer bound to the capture reagent is placed in the second zone of the biosensor device so that the analyte can bind to the composition in the second zone. In still further embodiments, the device further comprises a third zone adjacent to the first zone into which the fluid is absorbed after passing through the first defined area of the first zone. In further still embodiments, the first defined area has a dimension between the electrodes of 1.0 mm or less between determining the altered conductivity, or resistance.

The present invention still further provides a system for detecting an analyte in a fluid sample which comprises: (a) a biosensor device which comprises: a strip of a substrate having at least two zones wherein a (1) first of the zones comprises a first capture reagent for the analyte bound to or as a moiety of the substrate in a defined area and spaced apart electrodes defining sides of the defined area for providing an electrical bias to the defined area; and (2) a second of the zones comprising a fluid transfer medium for supplying a fluid to the first zone, wherein when there is a fluid sample comprising an analyte bound by a second capture reagent is provided in the second zone, the complex migrates to the first zone in the fluid transfer medium and the analyte is bound by the first capture reagent thereby altering a conductivity or resistance of the defined area in the first zone as measured between the electrodes wherein the second capture reagent is ferromagnetic particles bound to a conductive polymer bound to a capture reagent as a composition is provided in the second zone as a complex with the analyte; (b) electrical means for supplying an electrical bias between the electrodes or the detecting means; and (c) measuring means for determining a change in the conductivity or resistance of the first area before and after the complex bound in the first zone. In further embodiments, one or both of the capture reagents are antibodies. In further still embodiments, a pad adjacent to the second zone is provided for applying the fluid sample comprising the analyte prior to being introduced into the second zone. In still further embodiments, a pad for applying the fluid comprising the analyte which is applied prior to being introduced into the second zone. In further still embodiments, a pad adjacent to the second zone is provided for applying the fluid sample comprising the analyte prior to being introduced into the second zone.

The present invention still further provides the test kit wherein the biosensor device is a multi-array device comprising: a plurality of first zones on the single strip of substrate, each of the first zones having a first capture reagent with a different specificity bound to the single strip of substrate between electrodes to immobilize one of multiple analytes on the single strip of substrate so that each of the multiple analytes can be detected from the same sample on the single strip of substrate of the multi-array biosensor device. In further embodiments, the biosensor device is a multi-array device comprising: a plurality of first zones on the single strip of substrate, each of the first zones having a first capture reagent with a different specificity bound to the single strip of substrate between electrodes to immobilize one of multiple analytes on the single strip of substrate so that each of the multiple analytes are detected from the same sample on the single strip of substrate of the multi-array biosensor device. In still further embodiments, the biosensor device is a multi-array device comprising: a plurality of first zones on the single strip of substrate, each of the first zones having a first capture reagent with a different specificity bound to the single strip of substrate between electrodes to immobilize one of multiple analytes on the single strip of substrate so that each of the multiple analytes can be detected from the sample on the single strip of substrate of the multi-array biosensor device by providing a constant current and measuring generated voltage signals proportional to resistances across each of the first zones. In further still embodiments, the analyte bound to the second capture reagent is magnetically separated from a starting fluid sample before being provided in the second zone of the device. In further still embodiments, a magnet is used for separation of the complex of the ferromagnetic particles bound to the conductive polymer bound to the capture reagent bound to the analyte from a starting fluid sample.

The term "ferromagnetic particles" means an iron based particle which provides conduction or resistance. Preferably the particles are a nanoparticle having a dimension of 1 to 100 nanometers. Magnetic iron oxide ($Fe_2O_3$) is preferred as the particles.

The term "conductimetric" means that a signal is measured by means of a complex of the analyte linked directly or indirectly through a composition which is the ferromagnetic particles bound to a conductive polymer bound to a capture reagent in the biosensor device.

The term "magnetic" means able to be magnetized by an electrical field.

The term "resistance" means the electrical resistance usually measured in ohms.

The term "conductivity" means the current in amperes.

The term "analyte" means detecting a chemical or biological material including living cells in a sample which is detected by means of the biosensor device. The complexed analyte can be bound in solution, and preferably separated magnetically, and then applied to the device in a fluid or the analyte can be bound on the device and then migrate to a zone where there is a capture reagent.

The phrase "capture reagent" means (1) fluid mobile reagent which selectively binds to the analyte and a composition of the ferromagnetic particle labeled conductive polymer bound to a capture reagent which reacts with the analyte and (2) which is bound to or a moiety of the substrate in a detection zone of the device, and which also selectively binds to the analyte. Included within the term "capture reagent" are selective antibodies, DNA, enzymes, proteins and chemicals which bind the analyte in the biosensor device.

The phrase "conductive polymer" means any polymer which is conductive and which is fluid mobile when bound to an analyte, particularly when bound with a capture reagent. Included within the term "conductive polymer" are polyanilines, polypyrrole, polythiophenes and which are dispersible in water and are conductive because of the presence of an anion or cation in the polymer. Other electrically conducting polymers include substituted and unsubstituted polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, biomaterials, biopolymers, conductive carbohydrates, conductive polysaccharides, combinations thereof and blends thereof with other polymers, copolymers of the monomers thereof. The polyanilines are preferred. Illustrative are the conductive polymers described in U.S. Pat. Nos. 6,333,425, 6,333,145, 6,331,356 and 6,315,926. The polymers of the present invention do not contain metals in their metallic form (i.e. Me).

The term "substrate" means a non-conductive material, such as membranes, silicon, paper, plastic or glass, which serves as a support for the biosensor.

The term "zones" in reference to the first and second zones means a region of the biosensor where transfers in a fluid of a complex occur in the biosensor device.

The term "complex" means a coupling of the ferromagnetic particle bound to the conductive polymer bound to a complex bound to the analyte.

A "membrane" is a porous or non-porous material preferably made of nitrocellulose, fiber glass, cellulose, non-conductive biomaterials, and biopolymers, silicon, carbon nanotubes and other fluid transporting materials.

A "sandwich assay" is an assay which relies upon more than one capture reagent to selectively bind to an analyte. In the present biosensor device, one of the capture reagents is bound to or is a moiety of the substrate and the other is bound to or a moiety of the ferromagnetic particle bound to the conductive polymer bound to the capture reagent.

The term "multi-array" means a device for detecting multiple analytes simultaneously or sequentially from the same sample.

DESCRIPTION OF DRAWINGS

The patent or application file contains at least one drawing executed in color. Copies of this patent or patent application publication with color drawing(s) will be provided by the Office upon request and payment of the necessary fee.

FIGS. 2A, 2A1, 2B, 2B1, 2C, 2C1 show plan and side views respectively of the biosensor device 10 and the sequence of detection by antibodies (Y) bound to the signal generation membrane 12 and the ferromagnetic particles bound to the polyaniline labeled antibody (2B1 at membrane 17). After loading the sample on the application membrane 11, the solution flows up to dissolve the ferromagnetic particles bound to the polyaniline-labeled antibody in 2A and 2A1 (T). The arrow indicates the direction of flow. Binding between antigen and labeled antibody takes place in 2B and 2B1. The binding complex moves to NC membrane 12, and then reacts with the immobilized antibody to generate an electrical signal in 2C and 2C1.

FIG. 3 is a plan view of a device 20 with multi-array detection. The electrodes 22A to 22E that need to be covered with silver paste. Regions or arrays 21A to 21D with width of 20 μm are sites for immobilizing different types of antigen-specific antibodies (a, b, c and d) on signal generator membrane 23.

FIG. 6A shows the multimeter 19 electrically connect to the device 10.

Figures 1A, 1B:
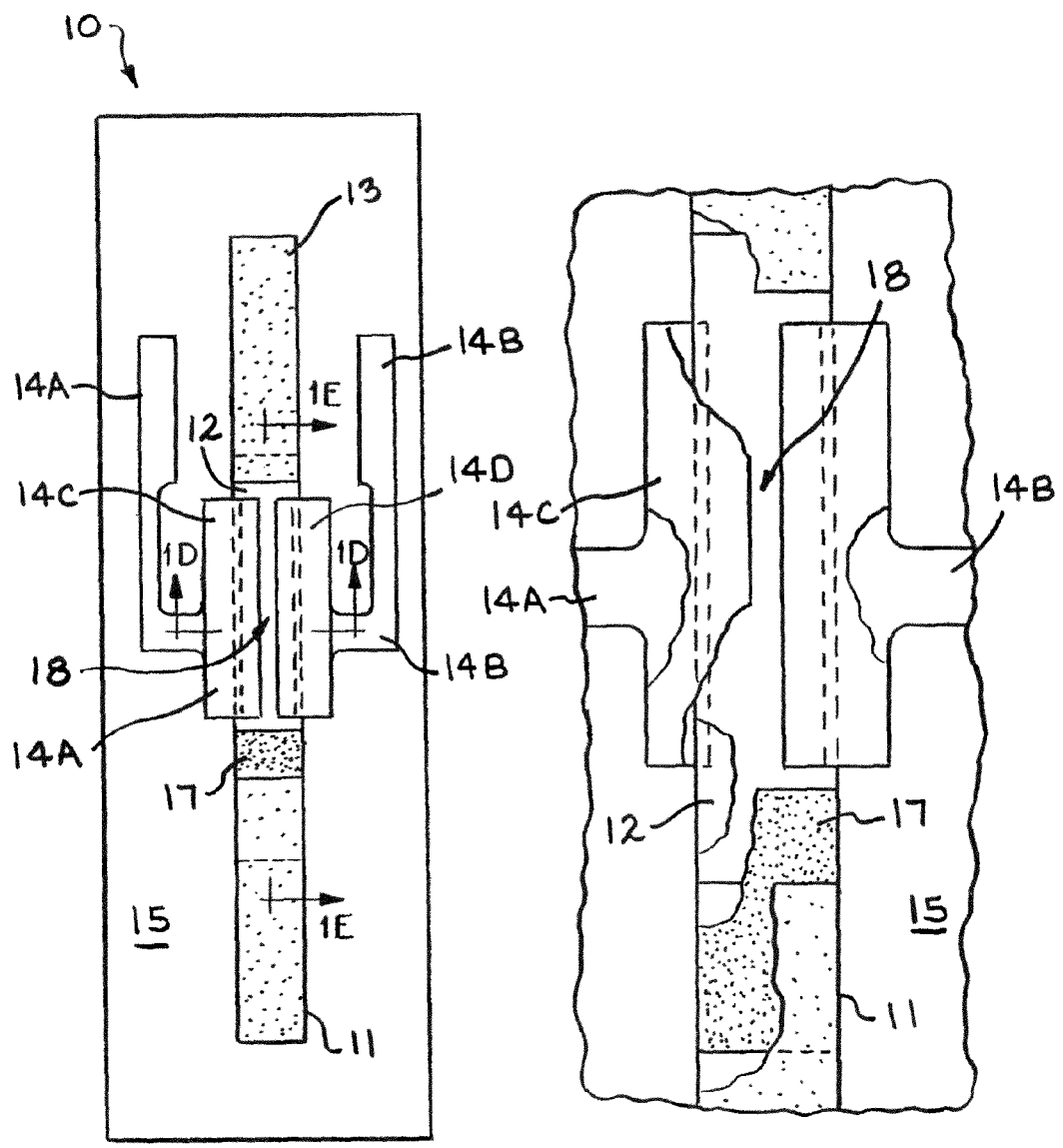
FIGS. 1A and 1B are plan views and FIG. 1C is a perspective view of a single unit or array of one embodiment of the conductimetric biosensor device 10 with an application membrane 11 and signal generation membrane 12 between electrodes 14A and 14B. Signal generation membrane 12 is coated on each side with the electrodes 14A and 14B made of copper and silver paste 14C and 14D, preferably 0.5 mm apart, wherein the gap 18 between electrodes 14A and 14B is the site for antibody or probe, immobilization of the analyte. The ferromagnetic particle bound conductive polymer-labeled antibody supporting membrane 17 is connected to the sample application membrane 11.

DESCRIPTION OF PREFERRED
EMBODIMENTS

Development of a conductometric biosensor for detecting pathogenic microorganisms and toxins using nanomagnetic polyaniline.

A specific objective of this invention is to demonstrate the use of a ferromagnetic particles bound to polyaniline polymer bound to an antibody (Magnetic polyaniline-capture reagent) in a lateral flow based conductometric biosensor. The Examples provide the preparation of polyaniline using magnetic iron (III) oxide nanoparticles, conjugation of the magnetic polyaniline with antibodies specific to a target antigen; and use of magnetic polyaniline in the biosensor.

Advantages: The use of an iron oxide nanoparticle polyaniline-capture reagent offers several advantages over the existing form of the lateral flow based biosensor. One embodiment of the biosensor device (which is preferably disposable) is comprised of four membrane pads, sample application pad, conjugate pad, capture pad and absorption pad. Ferromagnetic particles bound to the conductive polyaniline particles are conjugated with antibodies and applied to the conjugate pad and a second set of capture antibodies are bound to the capture pad. The working principle involves flow of liquid sample containing antigens in this embodiment form the sample application region to the conjugate region by capillary action to form an initial antigen antibody complex which is again carried to the capture region to form a sandwich complex, where the ferromagnetic particles bound to the conductive polyaniline particles generate a current signal between electrodes that is recorded.

In a second preferred embodiment, the magnetic polyaniline allows the biosensor to be used without the requirement of the conjugate membrane pad. The magnetic polyaniline is conjugated with antibodies and is applied directly to the liquid samples containing the antigens before being applied to the biosensor. The antigen forms complex with the antibody-magnetic polyaniline conjugates which is then concentrated with the help of a magnet on the container. The concentrated antigen-antibody-magnetic polyaniline complex is removed in a wash fluid and then applied to the biosensor device for measurement of the current signal. The magnetic nature of the polyaniline provides the following advantages: (1) use of the conjugate membrane pad is no longer required, magnetic nature of the ferromagnetic particles bound to the polyaniline allows concentration as the antigens from complex samples which might pose the problem of matrix interference in the biosensor and (2) biosensor sensitivity to application of concentrated antigen-antibody-polyaniline complex to the biosensor device.

EXAMPLE 1

FIGS. 1 to 6A

Reagents:

Aniline, glutaraldehyde, N,N Dimethylformamide (DMF), Tween-20, tris buffer, phosphate buffer, phosphate buffer saline (PBS) were purchased from Sigma-Aldrich (Missouri). Antibodies (Rabbit anti-$E.\ Coli\ O$157:H7) were obtained from Biodesign (Maine). Nitrocellulose (NC) membrane 12 with 8 μm pore size and flow rate of 160 sec per 4 cm, and cellulose membrane 13 were purchased from Millipore (Massachusetts). Fiber-glass membrane 11 grade G6 were also obtained from Millipore. Silver Kwik-stik pen for electrodes 14C and 14D was supplied from SPI (Pennsylvania). Other reagents used were of analytical grade. All chemicals and diluents were prepared with doubly deionized water with conductivity below 0.1 μS/cm.

Antibody Labeling with Polyaniline

A water-soluble polyaniline was synthesized with magnetic iron nanoparticles as the ferromagnetic particle by following a standard procedure of oxidative polymerization of aniline monomer in the presence of ammonium persulfate. A mixture of the antibody and magnetic iron particle labeled polyaniline was left to react for 30 minutes. The conjugate was then precipitated by centrifugation (13000 rpm for 3 min) using 0.1 M Tris buffer as the blocking reagent. The conjugated antibody was diluted in 0.01 M LiCl.

1.2 Fabrication of Silver Electrodes

For electrical connection, a silver paste pen was used to make the electrodes 14C and 14D on the capture nitrocellulose (NC) membrane as the signal generation membrane 12. The silver paste 14C and 14D was applied liberally to ensure consistency in the flow of electricity between the copper electrodes 14A and 14B. The distance between the two silver electrodes 14C and 14D was in the capture region and was 0.5 mm wide. To increase detection sensitivity, the distance between the electrodes can be reduced to 2-20 μm by using microinterdigitated technology.

Immobilization of Antibody on the Capture Membrane

Affinity purified antibody was directly immobilized between the two silver electrodes of the NC membrane by the following steps. First, the NC membrane was saturated in 10% (v/v) methanol for 45 minutes and left to dry. The surface of the membrane was then modified by immersing it in 0.5% (v/v) glutaraldehyde as a linking agent for 1 hour. After drying, 2.5 μl of 0.5 mg/ml of antibody was pipetted on the membrane site, and incubated at 37NC for 1 hour. Inactivation of residual functional groups and blocking was carried out simultaneously by incubating the membrane with 0.1 M Tris Buffer, pH 7.6, containing 0.1% Tween-20 for 45 minutes. The membrane with the linked antibody was left in the air to dry before proceeding to the next step.

Construction of One Unit of the Conductimetric Biosensor Device

Figure 1C:
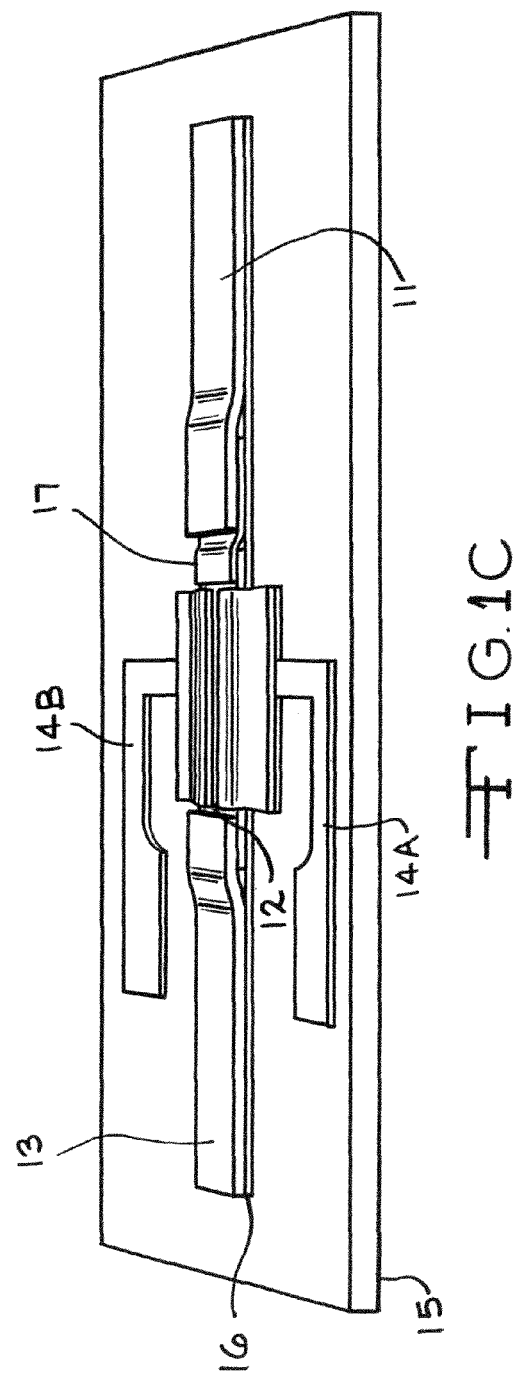
Figure 1D:
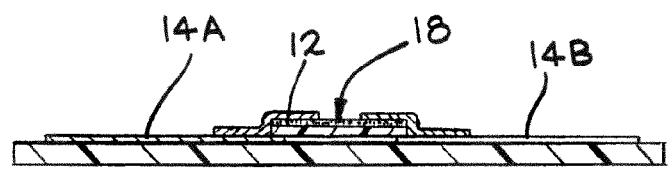
FIGS. 1D and 1E are cross-sections along lines D-D and E-E of FIG. 1A.
Figure 1E:
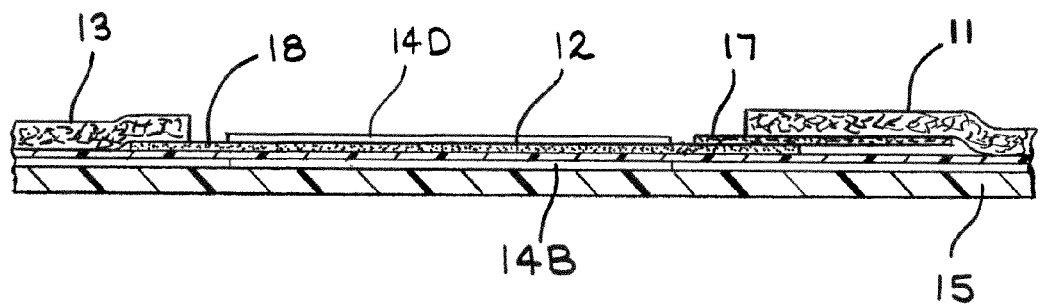

The biosensor device 10 (FIG. 1) was designed with three membranes: application membrane 11, capture or signal generation membrane 12, membrane 17 containing the conductive polymer labeled antibody and absorption membrane 13. The system was constructed as shown in FIGS. 1A, 1B and 1C with the fiber-glass (FG) membrane 11 (5×10 mm) for sample application, the nitrocellulose (NC) membrane 12 with immobilized antibody (5×20 mm) coated with silver electrodes 14C and 14D to capture the analyte, and cellulose membrane 13 (5×20 mm) for absorption of sample. The membranes 11, 12 and 13 were arranged in the order mentioned and attached onto a wafer substrate 15 using a double-sided tape 16 (FIG. 1C). Eight μl of conductive polymer (polyaniline)-labeled antibody was placed on the membrane 17 as shown in FIG. 1A.

1.5 Analytical Procedure

Before applying the sample onto the application membrane (or pad) 11, the resistance between the silver electrodes 14C and 14D was noted. To begin the test as shown in FIGS. 2A and 2A1, 0.1 ml of sample (containing the antigen) was dropped onto the application membrane 11. By capillary action, the solution flowed up the conjugate membrane 17 and dissolved the ferromagnetic particle bound polyaniline-labeled antibody (FIGS. 2B and 2B1). Antibody-antigen reaction occurs and forms a complex. This complex was carried up by the migrating fluid into the capture region of membrane 12 containing the immobilized antibody (FIG. 2C, 2C1). A second antibody-antigen reaction occurred and formed a sandwich-type immune complex. The polyaniline in the sandwich complex formed a molecular wire, bridges the two silver electrodes 14C and 14D, and formed the circuit, thus generating an electrical signal. The generated signal was measured using a digital multimeter 19 (FIG. 6A) 2 to 10 minutes after the sample was applied on the application membrane 11. The concentration of the analyte was inversely proportional to the resistance across the electrodes 14C and 14D.

Without any sample, the resistance across the electrodes 14A, 14C and 14B, 14D was infinite. After sample application, the generated signal fluctuated for the first few seconds while the sample flowed by capillary action to the absorption membrane 13. Dispersion time from sample membrane 11 to absorption membrane 13 was less than one minute. When enough antigens were present, the signal stabilized and was recorded. The magnitude of signal was inversely related to antigen concentration, that is the resistance signal decreased with increasing antigen concentration. The biosensor device 10 was calibrated with the enrichment broth as the blank sample. The presence of antigen was confirmed by the standard plating method according to approved Food and Drug Administration protocol.

Figure 5:
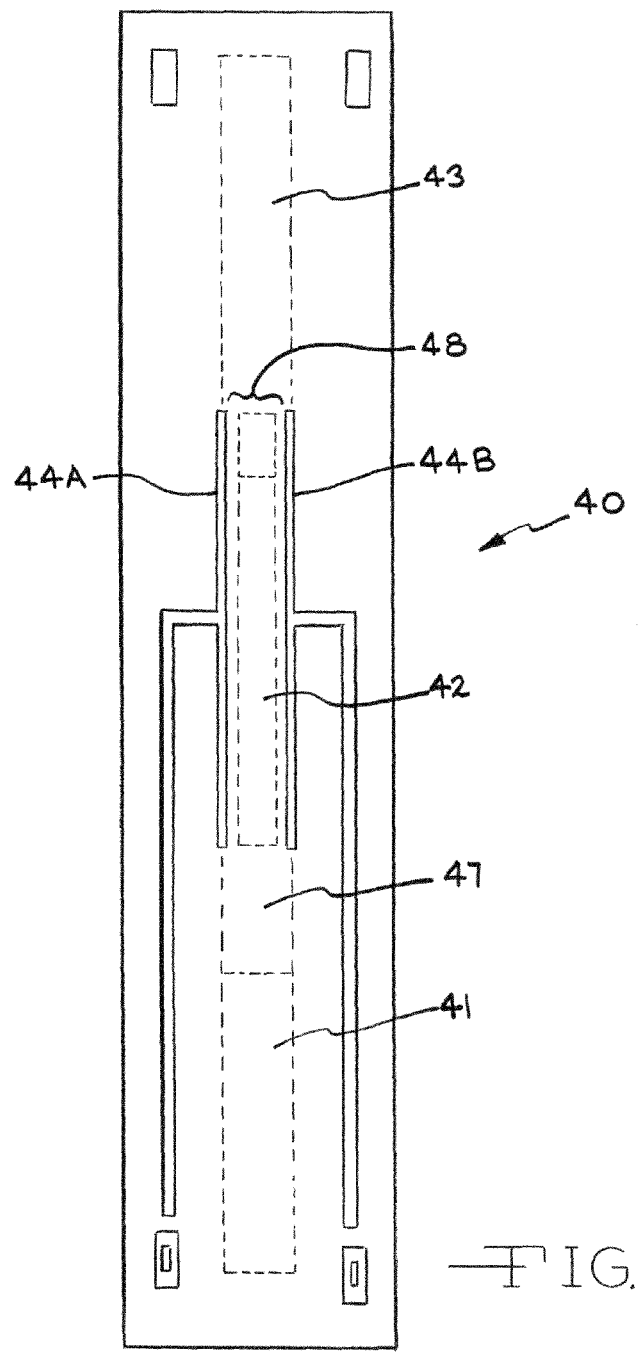
FIG. 5 is a plan view of the embodiment of the device 10 of the present invention on a wafer substrate as a non-conductive support and with a copper coating 14A and 14B connecting the electrodes 14C and 14D on membrane 12. The relative dimensions are shown.
Figure 6:
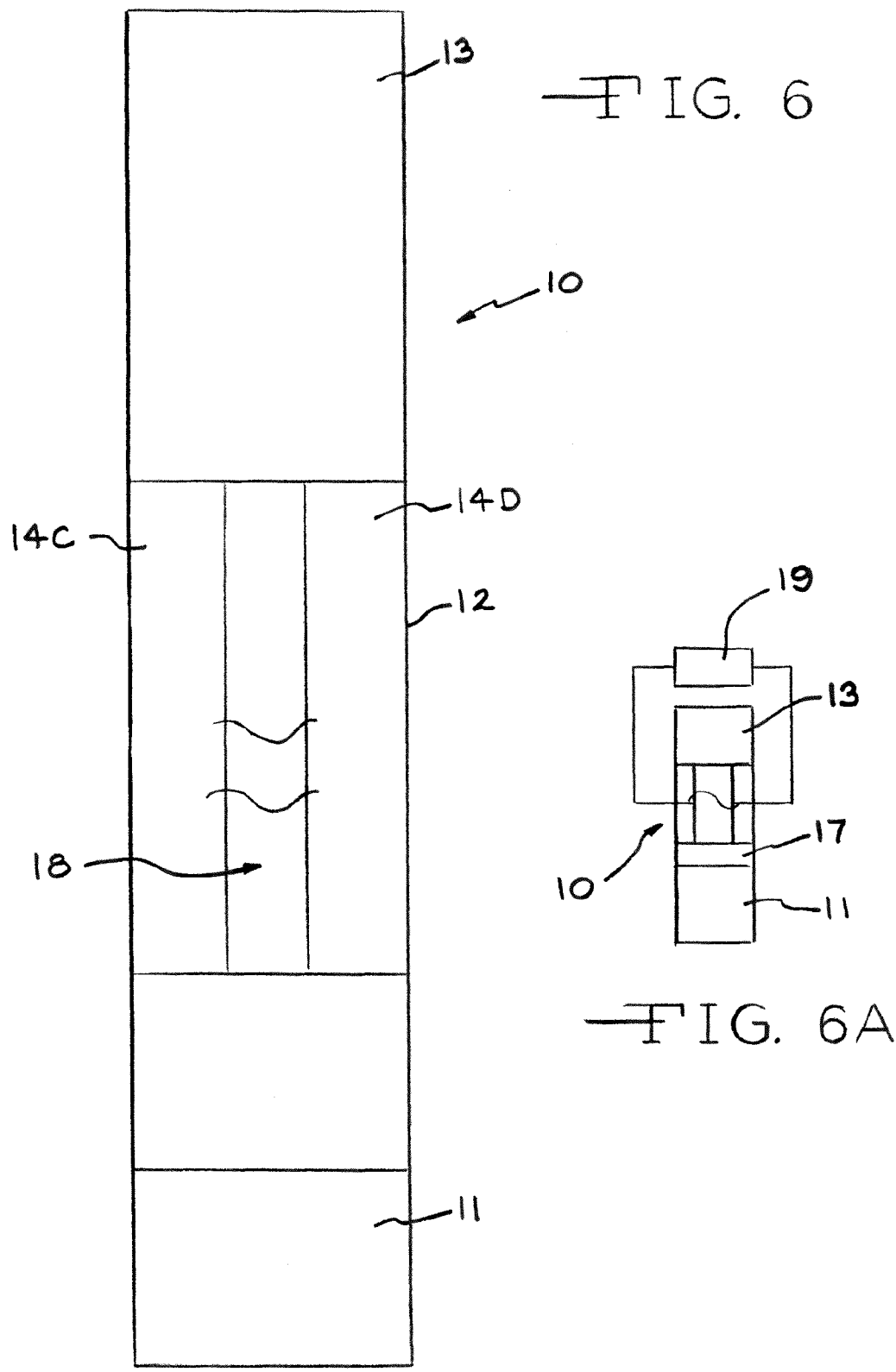
FIG. 6 is an enlarged view which shows the various areas of the strip 10 of FIG. 5 and the function.

The specific construction of biosensor device 10 is shown in FIG. 5. The gap 18 was 5 mm inside×30 mm long. The polyaniline membrane 17 (dotted lines) with the conjugated antibody was 10 mm long×5 mm wide in the gap 18. The sample membrane 11 was fiber glass and measured 5 mm wide and 10 mm long.

The device 10 was prepared as follows:

Procedure:

1. Construction of the Analytical Systems
   1. Prepared the model as shown in FIG. 1B above using nitrocellulose (NC) membrane 12 from Millipore (Massachusetts).
2. Immobilized the Antibody
   1. The membrane 12 was washed 3 times with distilled water, then treated with 10% (v/v) methanol for 30 minutes and left to dry.

Prep:

Nitrocellulose (NC) membranes were cut in to the smaller pieces (6-7 cm) to fit a petri dish. 10 ml methanol is dissolved in 100 ml of distilled water.

2. The surfaces were modified by immersing them in 0.5% (v/v) glutaraldehyde sol for 1 hour and wash with distilled water.

Preparation:

0.5 ml glutaraldehyde was mixed with 100 ml distilled water. Approximately 1 ml of the solution was applied on each piece and let it be absorbed on the entire surface.

3. 0.5 mg/ml antibody was diluted into 0.02 mol phosphate buffer (PB) at pH 7.4, applied on the membrane 12, and incubated for 1 hr in the sealed container to maintain 100% humidity to immobilize the antibody.

Preparation:

1. Made 0.02 mol phosphate buffer (PB)

$0.02 \times \text{formula weight}(FW)(\text{dibasic}) \times 80\%$ (of total Volume required)

$0.02 \times FW(\text{monobasic}) \times 20\%$ (of total Volume required)

Desired pH was adjusted with 1 N NaOH

After applying the antibody, the petri dish was sealed with parafilm to ensure 100% humidity.

4. The membrane was incubated in 100 mM tris buffer, pH 7.6 containing 0.1% (v/v) Tween-20 for 45 minutes and then dried off.

Preparation:

Weighed 12.1 g of tris in 1 liter distilled water.
Adjusted the pH to 7.6
Autoclaved for 45 min
Added 1 ml of Tween-20

3. Conjugating Antibody and Polyaniline Polyaniline Polymerization 5 ml of 0.4 M of iron (III) oxide nanopowder ($Fe_2O_3$) FW (159.69) aniline were mixed with 40 ml of 0.2 mM ammonium persulfate (APS), and diluted into 80 mL of 1M HCl, and reacted for 30 mins.

Preparation:

Mixed 0.188 ml of aniline in 5 ml distilled water in a beaker
Added 8 ml of 1M HCL in 80 ml distilled water in another beaker
Added 4.564 gm of APS in 100 ml distilled water 2. Wash with 5% ammonia hydroxide to rinse out excess HCl Prep The initial construction was 30% by volume
Need 5%, therefore do 1:6 dilution,
Mix 10 ml ammonia hydroxide and 50 ml water 3. Filtered the product from the filter paper.
4. Product was dissolved in 5 ml dimethyl formamide (DMF).
5. Undissolved product was eliminated by filtration.
6. The soluble polymer was precipitated by adding 2 mL 2 M HCl in DMF Preparation:

2 ml of HCl in 10 ml distilled water

7. After filtration, residual solvent was evaporated.
8. The final protonated product was dissolved in phosphate buffer saline (PBS) containing 10% (v/v) DMF.

Antibody Preparation:

1. Antibody was used as supplied
2. Conjugation steps

Added 800 μl of 150 μg/ml antibody in 8 ml of 0.1 g/ml of magnetic iron oxide particle labeled polyaniline (PAN)
Let it to react for 30 mins.
Added 1 ml of 0.1M Tris 0.5% casein, left to react again for 30 mins
Spin at 13000 rpm for 3 min
Added 0.1M Tris 0.5% casein again and spin for another 3 min
The above procedure was carried out for 3 times
Lastly added 0.1% LiCl
Stored in the refrigerator when not in use Preparing the Conjugation Pad The conjugation, membrane 17 was soaked with the conductive polymer labeled antibody and left to air-dry.

EXAMPLE 2

Construction of Multi-Array

Figure 4:
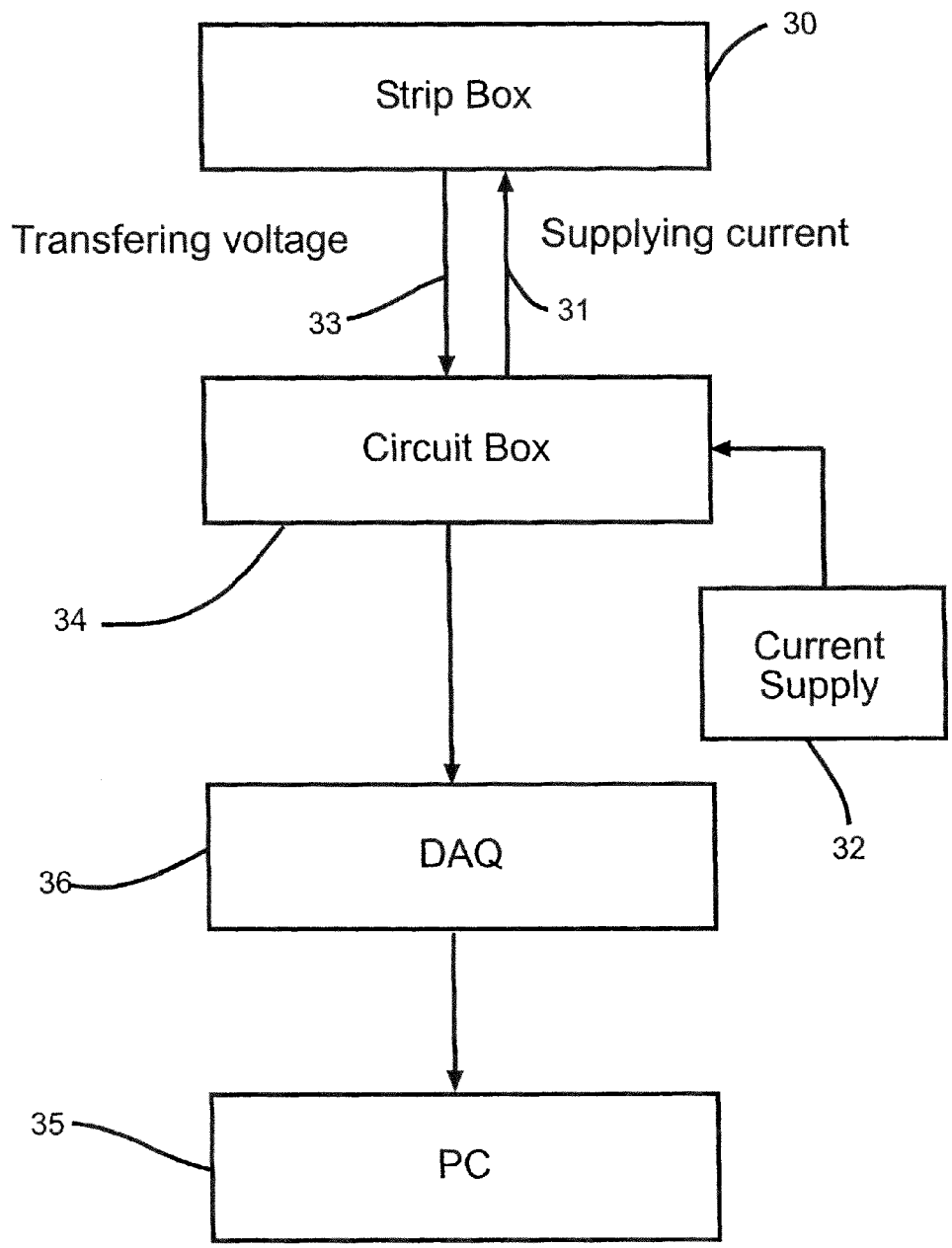
FIG. 4 is a schematic system for testing a single multi-array device 10, 20 or 100 including a box 30 into which the device 10, 20 or 100 is inserted.

More than one capture zone is designed on the NC capture membrane 20 as shown in FIG. 3, thus, multiple types of antibodies with different specificity can be immobilized on the membrane 20. FIG. 3 shows the design of the capture or signal region 23 with multiple regions 21A to 21D for antibody immobilization between electrodes 22A to 22E. As shown in FIG. 4, after sample application, the biosensor device 10 is inserted into the strip box 30. The lead wire 31 attached to the side of the box 30 induces a constant current from the power supply 32. The current flows across the capture or signal region 23 and generates a voltage signal 33, which is proportional to the changes of the resistance. The generated voltages are transferred through a circuit box 34 and stored in the computer 35 via the data acquisition 36.

Examples 1 and 2 show:

1. A reduced distance between electrodes to preferably less than 500 μm in order to increase desired sensitivity to 1-10 cfu;
2. Improved membrane materials to reduce detection time to less than 2 min; and
3. A multi-array system for multiple and simultaneous detection.

EXAMPLE 3

FIGS. 7 to 10 show a preferred embodiment of the present invention.

The biosensor device was used as a direct-charge transfer biosensor for the detection of *Bacillus anthracis* Sterne endospores. The biosensor detection was based on capillary flow of immuno-magnetically captured spores aided by the direct-charge transfer of the electrically-active nanomagnet resulting in the generation of an electric signal.

The nanomagnetic iron oxide polyaniline coated primary antibodies were used to concentrate target antigens from a liquid sample, and then applied directly to the biosensor device as shown in FIG. 5. The biosensor device used the lateral flow technique for movement of liquid sample from one membrane to another. The immuno-magnetically captured target antigens flowed from the application zone (region) 101 to the capture zone 102 of the biosensor where they were anchored by the bound secondary antibodies in the capture zone 102 resulting in the formation of a sandwich complex. The electro-magnetic polyaniline nanoparticles in the complex acted as a charge transfer agent between the electrodes and initiated a voltage-controlled 'ON' switch. This direct-charge transfer across the electrodes generated an electric signal which was being recorded in terms of resistance. The waste level was removed in the absorption region (zone) 103.

Thus a biosensor device using electrically-active nanomagnets as an immuno-magnetic seperator and concentrator was used for the detection of Bacillus anthracis spores and to evaluate the sensitivity and the specificity of the biosensor.

Materials and Methods: The preferred construction of the biosensor device involves the following steps:

Synthesis and characterization of PANi-$Fe_2O_3$— To synthesize the magnetic form of polyaniline, iron (III) oxide nanopowder ($Fe_2O_3$, FW 159.69) and aniline (FW 93.13) were dissolved in 1M HCl and stirred at ice temperature, as ammonium persulfate was added gradually. The polyaniline formed and bound to the nanopowder after reaction had occurred (evidenced by color change), and then the solution was filtered and washed. The resulting solid was allowed to dry and then crushed into powder. Magnetization of this PANi-$Fe_2O_3$ powder tested using a DC SQUID magnetometer (Superconducting Quantum Interference Device, Quantum Design). Conductivity of solid form (pellet) was measured with Pro4 four-point probe (LUCAS/SIGNATONE CORP., Gilroy, Calif.).

Preparation of biosensor-Nitrocellulose membranes (Millipore, Billerica, Mass.) were assembled and cut to form 5 mm-wide conductometric biosensors, consisting of a sample pad, a capture membrane, and an absorption pad. Surfaces were washed and dried and the capture membrane was coated with antibodies to the target pathogen. A silver conductive pen was used to create electrodes on each edge of the capture membrane. The biosensor strip was placed on a wafer between two copper electrodes which were connected to the electrodes on the strip using the silver pen. The copper electrodes were connected to a bench-top digital multi-meter.

Conjugation of antibodies with PANi-$Fe_2O_3$— PANi-$Fe_2O_3$ powder and target-specific antibodies were combined and incubated in Na-phosphate buffer to directly bind the antibodies to the polyaniline. Centrifugation and reconstitution was used to remove unconjugated antibodies.

Bacillus Sample Preparation—Seven serial dilutions were performed beginning with pure culture of the target antigen. A solution was formed containing 20% PANi-$Fe_2O_3$-antibody conjugate and 10% antigen of a specified dilution. After a brief incubation period the solution was exposed to a magnetic field which held the PANi-$Fe_2O_3$— antibody-antigen complexes in place while supernatant was removed, eliminating any unbound antigens. The particles were reconstituted and applied to the biosensor for testing.

Signal Detection—As the sample flows from the biosensor's sample pad across the capture membrane, vacant binding sites on the antigen cells fasten to the antibodies which are adhered to the membrane. In this way the PANi-$Fe_2O_3$— antibody-antigen complexes form a conductive bridge connecting the electrodes one each side of the capture membrane. The resistance value across the capture membrane is read from the digital multi-meter.

Control and Validity—For each cell dilution of the antigen tested, multiple trials are carried out. In each trial, the resistance is recorded at 2 minutes, 4 minutes, and 6 minutes after the sample was applied. A positive control sample consisting of PANi-$Fe_2O_3$-antibody with no antigen is also tested. The supernatant and conjugate obtained for each dilution are plated in order to determine the approximate antigen cell count, and verify that conjugation is occurring.

Thus, (1) Polyaniline was synthesized by the oxidative polymerization of aniline monomer in the presence of gamma iron (III) oxide ($\gamma$-Fe2O3) nanoparticles.

(2) Four different weight ratios of $\gamma$-Fe2O3 to aniline, 1:0.1, 1:0.4, 1:0.6 and 1:0.8 were maintained during the polymerization procedure.

(3) A Quantum Design MPMS SQUID (Superconducting quantum information device) magnetometer was used for magnetic characterization and room temperature hysteresis measurements of the synthesized electromagnetic polyaniline.

(4) The structural morphology of the synthesized polymer was studied by Transmission Electron Microscope (JEOL 100CX).

Biosensor Application

Figure 7:
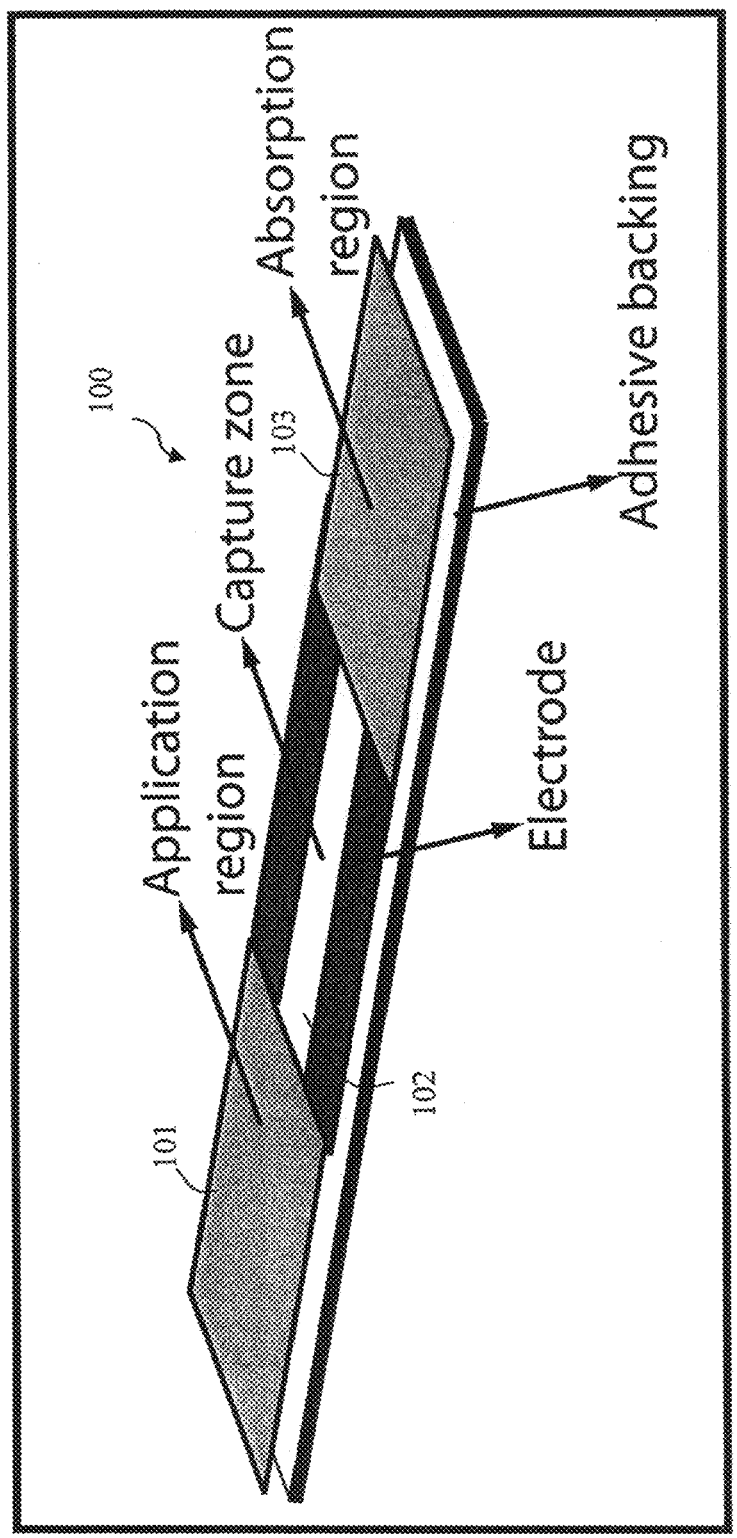
FIG. 7 is a perspective view of another embodiment of the conductimetric device 100 of the present invention wherein the magnetically isolated or separated analyte bound to the captive reagent bound to the conductive polymer bound to the capture reagent-analyte complex is applied to the application region or zone 101 and flows to the capture zone 102 and waste fluid goes to the absorption region or zone 103.

Biosensor Preparation:

(1) The biosensor architecture as shown in FIG. 7 had dimensions of 60 by 5 by 2 mm3, and was comprised of three membrane pads: application pad, capture pad and absorption pad as in FIG. 5.

(2) The application, capture and the absorption pads were attached to an adhesive backing on an etched copper wafer with silver electrodes fabricated 0.5 mm apart on the capture zone.

(3) The capture zone had rabbit polyclonal antibodies to Bacillus anthracis spores immobilized on its surface.

Immuno-magnetic Concentration:

(1) The polyaniline nanoparticles were coated with mouse monoclonal antibodies to Bacillus anthracis spores (clone 2C3).

(2) The antibody and the polymer nanoparticle concentration in the prepared conjugates were maintained at 150 µg/ml and 100 mg/ml respectively.

(3) 200 mg of the polymer coated antibodies were incubated with different spore concentrations of Bacillus anthracis in 0.1% peptone water for 10 min.

(4) The immuno-magnetically captured spores were separated by a magnetic separator and washed and resuspended in 0.1% peptone water.

(5) 100 µl of the captured spore solution was applied to the direct-charge transfer biosensor and the electric signal generated across the silver electrodes was monitored for 6 min.

Figures 8A, 8B, 8C, 8D:
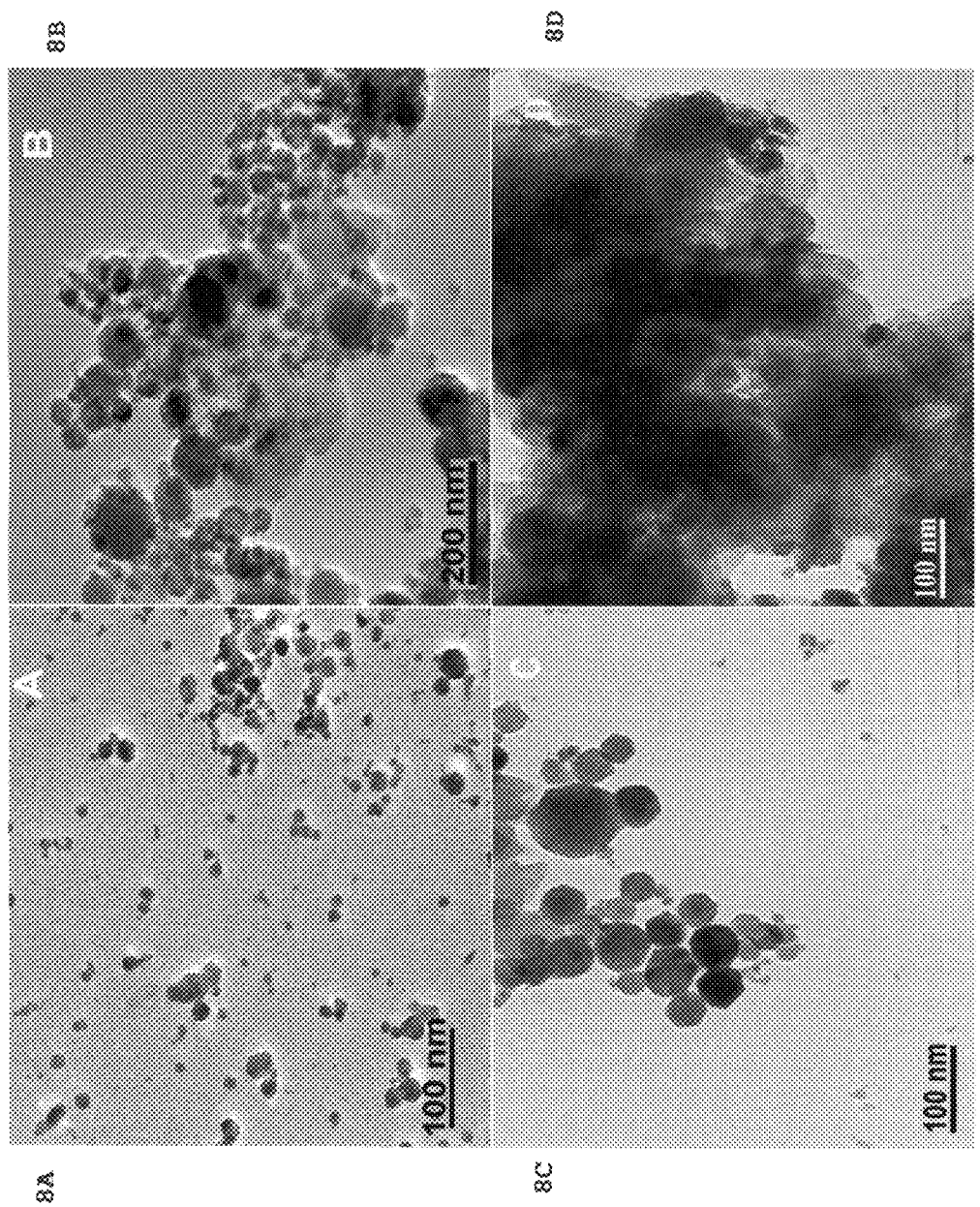
FIGS. 8A to 8D show TEM images of different weight ratios of polyaniline-$\gamma Fe_2O_3$ complexes A. 1:0.1, B. 1:0.4, C. 1:0.6, D. 1:0.8.

Results & Discussion (1) The synthesized nanomagnets had average diameters in the range of 50 and 200 nm as shown in FIG. 8.

Figure 9:
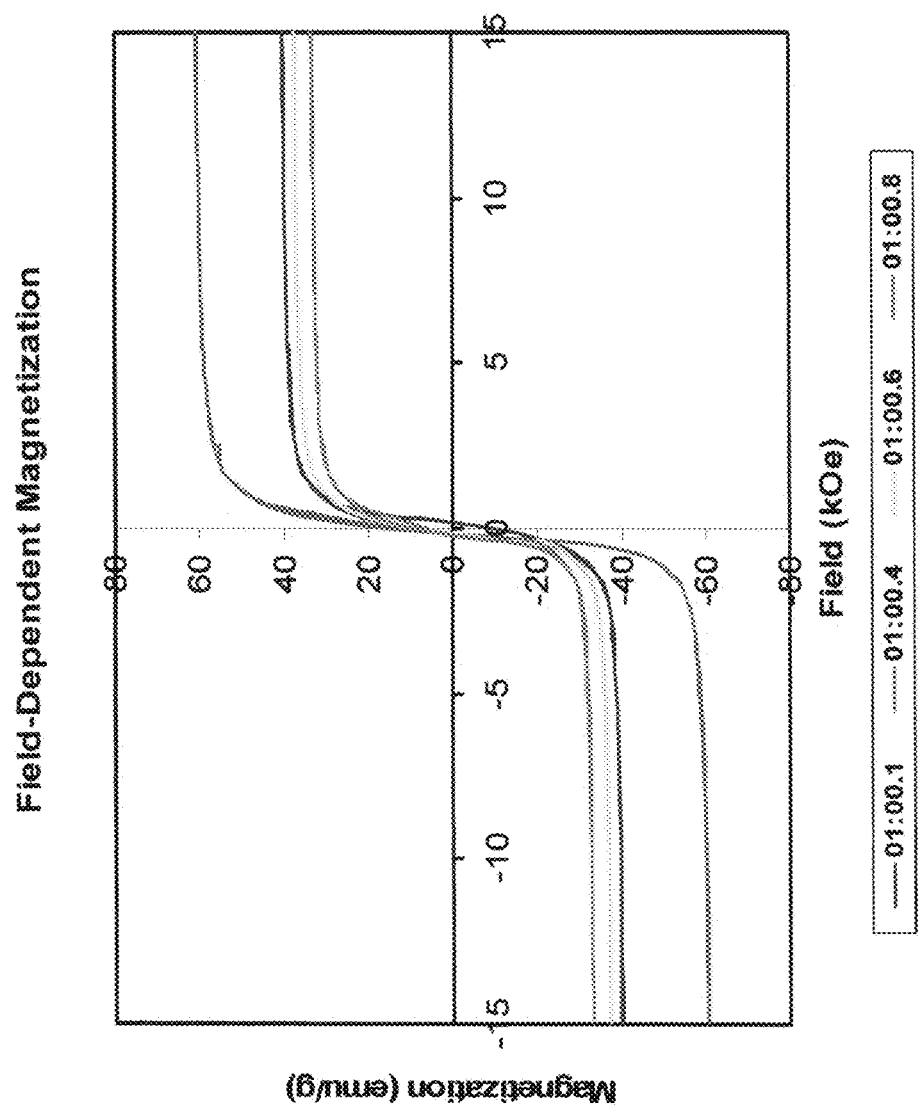
FIG. 9 is a graph showing field dependent magnetization hysteresis measurements of the different polyaniline-$Fe_2O_3$ complexes of FIGS. 8A to 8D.

(2) The saturation magnetization values for the four different weight ratios of the nanomagnetic polymer were between 61.1 and 33.5 emu/g as shown in FIG. 9.

(3) The synthesized nanomagnets showed low values of coercivity and retentivity.

Biosensor Sensitivity & Specificity:

(1) The sensitivity performance of the four different nanomagnet preparations were evaluated in a Bacillus cereus biosensor, where the preparation with a weight ratio of 1:0.6 showed the best performance in terms of sensitivity and signal generation.

Figure 10:
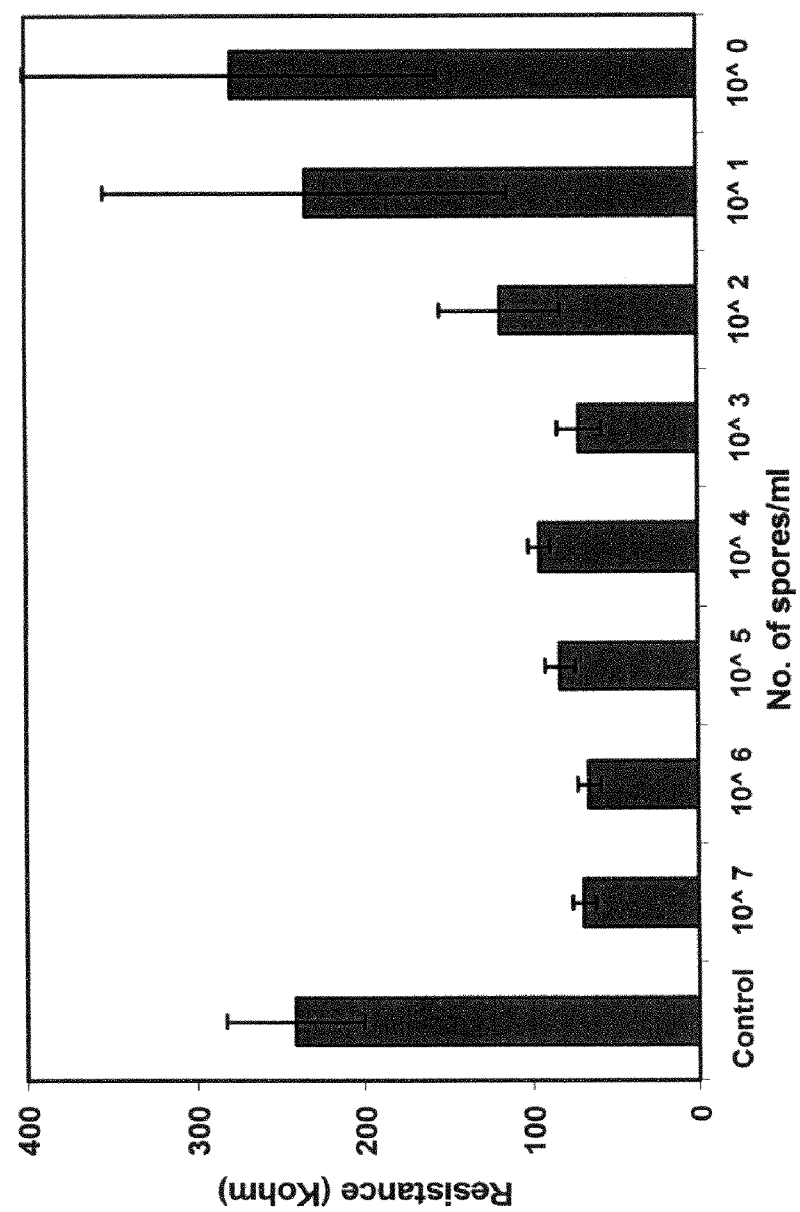
FIG. 10 is a graph showing *Bacillus anthracis* biosensor sensitivity in relation to the number of spores.
Figure 11:
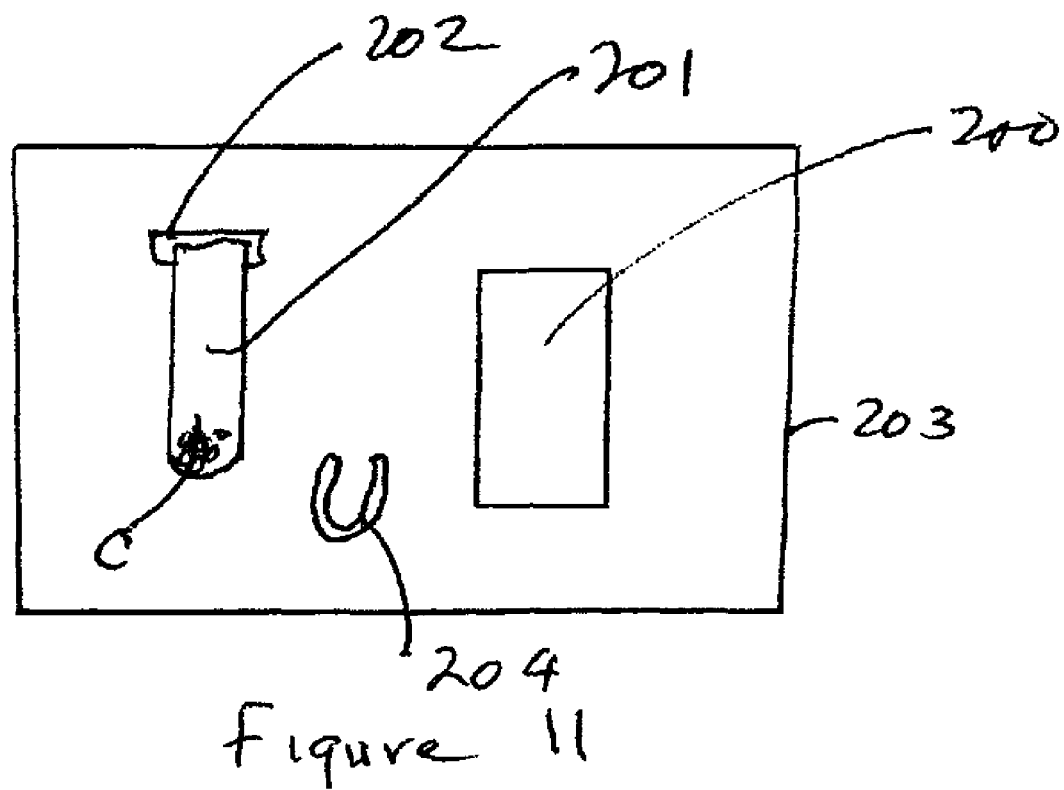
FIG. 11 shows a test kit with a biosensor device 200 and a container 201 with a cap 202 containing the composition C of the ferromagnetic particles bound to the conductive polymer bound to the capture reagent in a pouch on the container 203 with a magnet 204.

(2) The biosensor was able to detect Bacillus anthracis spores at a concentration as low as $4.2 \times 10^2$ spores per ml as shown in FIG. 10.

The specificity study of this biosensor was performed in pure cultures of *E. coli* CN13 and was found to be specific for *Bacillus anthracis* spores.

An electrically-active nanomagnet based biosensor was developed. The lowest detection limit of the biosensor for *Bacillus anthracis* spores was $10^2$ per ml. Detection was completed in 6 min.

Thus the present invention uses novel biologically enhanced electrically-active magnetic (BEAM) nanoparticles. The magnetic properties of the nano-BEAM particles serve the purpose of concentrating and separating specific targets from complex sample matrices, while the electrical properties of the nano BEAM particles are exploited for biosensing applications.

The novel application of biologically enhanced electrically-active magnetic polyaniline nanostructures as compositions as a magnetic concentrator and a transducer in biosensing applications has been described.

Present literature does not show any such application of electrically-active magnetic polyaniline nanostructures as compositions. These EAM nanostructures as compositions can mimic the function of magnetic beads widely used as a separator for immunomagnetic separation in immunoassays, for hybridization with nucleic acid probes as capture reagents, as templates in PCR and the like which have already been well reported in the literature. In addition to the function mentioned above, the electrical and the magnetic properties of the nanostructures or composites can also be exploited to be used as molecular transducers in biosensors. Some of the major advantages of the compositions are:

1. Ability to perform the dual function of a magnetic concentrator as well as a biosensor transducer.
2. Ability to achieve faster assay kinetics since the compositions are in suspension and in close proximity to the target.
3. Increased surface area for the biological events to occur.
4. Minimized matrix interference due to the improved separation and washing steps.
5. Ability to magnetically manipulate the magnetic nanomaterials by using permanent magnets or electromagnets.
6. Ability to avoid complex pre-enrichment, purification or pre-treatment steps necessary in standard methods of detection.
7. Ability to design cheap, sensitive, highly specific and rapid detection devices for diverse targets by using different biological modifications
8. Ability to design different rapid detection devices using both electrical and magnetic properties of the BEAM nanoparticles.

EXAMPLE 4

Synthesis—The electrically-active magnetic (EAM) nanoparticles were synthesized by the oxidative polymerization of aniline monomer made electrically active by a cid doping (addition of small quantities of foreign atoms, particularly protonating acids such as hydrochloric acid and sulfuric acid, that can release protons) in presence of gamma iron (III) oxide nanoparticles ($\gamma Fe_2O_3$) (Sharma R; Lamba S; Annapoorni S; Sharma P; Inoue A; (2005), Composition dependant magnetic properties of iron-oxide polyaniline nanoclusters. Journal of Applied Physics, 97 (1), 14311-14316). The $\gamma Fe_2O_3$ nanoparticles were obtained from a commercial source Sigma-Aldrich (St. Louis, Mo.). The $\gamma Fe_2O_3$ nanoparticles were first dispersed in a mixture of 50 ml 1M HCl, 10 ml de-ionized water and 0.4 ml of aniline. The above mixture was sonicated for 1 h in an ice bath in order to disintegrate the agglomerated nanoparticles. This was followed by a slow drop-wise addition of the oxidant (ammonium persulfate) to the above mixture with continuous stirring. The ice bath reaction was continued for an additional 4 h. The final product obtained was filtered, followed by repeated washings with 1M HCl, methanol and diethyl ether and dried at room temperature for 48 h to obtain a dark green powder. Four different weigh ratios of $\gamma Fe_2O_3$ to aniline monomer (1:0.1, 1:0.4, 1:0.6 and 1:0.8) were synthesized using the above procedure.

Magnetism measurement. A Quantum Design MPMS SQUID (Superconducting quantum information device) magnetometer was used for magnetic characterization and room temperature hysteresis measurements of the synthesized electromagnetic polyaniline. For the hysteresis loop measurement, the magnetic samples were subjected to a magnetic field cycling between +20 kOe and −20 kOe, while the temperature was maintained constant at 300K. The saturation magnetization values of each sample was determined in emu/gm and compared with that of pure gamma iron-oxide particles. The coercivity and retentivity of the magnetic nanoparticles were also studied form the room temperature hysteresis measurements in order to study the presence of super paramagnetic behavior in these samples.

Electrical conductivity measurements. The electrical conductivity of the synthesized magnetic nanoparticles was evaluated in both liquid and solid forms. For conductivity measurements in liquid form, the magnetic nanoparticles were dissolved in appropriate solvents and the conductivity was measured with the help of a conductivity meter (Acorn® TDS 5 Meter). For solid conductivity was measured with the help of a Four Point Probe (Lucas/Signatone Corporation, Pro4; CA, USA).

Structural Characterization. The structural morphology of the EAM nanoparticles were studied using both Transmission Electron Microscopy (JEOL 100CX II) and Scanning Electron Microscopy (JEOL 6400V) (Japan Electron Optics Laboratories). The shapes and sizes of the nanoparticles were estimated using the electron microscopic images. Crystalline or amorphous nature of the nanoparticles was also studied by Selected Area Electron Diffraction using the JEOL 2200FS 200 kV field emission TEM. X-Ray Energy Dispersive Spectroscopy was also carried out for the EAM nanoparticles using the JEOL 2200FS TEM for determining the percentage composition of the polymer and the gamma iron-oxide nanoparticles in the synthesized nanopolymers. The particle size distribution of the nanoparticles will be studied by measuring the zeta potential using a ZetaPALS analyzer (Brookhaven Instruments). UV-VIS spectral characterization of the nanoparticles will be done using a UV-VIS-NIR Scanning Spectrophotometer (UV-3101PC, Shimadzu, Kyoto, Japan).

Biologically enhanced EAM (BEAM) nanoparticles. The synthesized EAM nanoparticles have the potential to be biologically enhanced by a wide variety of biological materials like antibodies, DNA, aptamers, enzymes, whole cells etc.

Antibodies—The EAM nanoparticles were linked with antibodies to a specific target by incubating the antibodies in a suspension of polyaniline in phosphate buffer (pH-7.4) containing dimethylformamide and lithium chloride for 1 h. After incubation, the biologically modified EAM nanoparticles were treated with a blocking solution and washed and collected by centrifugation at 13000 rpm for 3 min. The BEAM nanoparticles thus obtained were suspended in appropriate buffer and stored at 4° C.

The polyaniline nanoparticles were immersed in a specific oligonucleotide solution of appropriate concentration containing 0.1 mol l$^{-1}$ 1-ethyl-3-(3-dimethylaminopropyl-1)-carbodiimide (EDAC) and 10 mmol l$^{-1}$ acetate buffer (pH-5.2) for 10 h with gentle stirring in an incubator shaker at room temperature (Zhu N; Chang Z; He P; Fang Y; (2006). Electrochemically fabricated polyaniline nanowire-modified electrode for voltammetric detection of DNA hybridization. Electrochimica Acta, 51, 3758-3762). The ssDNA bound nanoparticles were then separated by a magnetic separator (Spherotech, IL, USA) and washed with a 0.1% SDS phosphate buffer (pH-7.3) for 5 minutes to remove the unbound DNA probes. Finally, the DNA bound nanoparticles were suspended in PBS (pH-7.4) and stored at 4° C.

Enzymes and whole cells—The synthesized EAM nanoparticles will also be modified with enzymes and whole cells specific to certain targets using appropriate procedures.

Magnetic separation using BEAM nanoparticles. The nano BEAM particles were used to concentrate different specific targets from pure solutions and complex matrices. Approximately 200 mg of the nano BEAM particles were used to separate the specific targets followed by an incubation of the nanoparticles with the targets. The magnetic materials with the bound targets were captured by a magnetic separator and the presence of the targets was confirmed by standard conventional techniques.

Biosensor Application The synthesized nano BEAM particles can be used as a transducer for diverse biosensor applications exploiting both the electrical and magnetic properties of the material. The biosensor is an analytical device that integrates a biological sensing element with an electrical transducer to quantify a biological event (for e.g. an antigen-antibody reaction) into an electrical output. The biological sensing elements include enzymes, antibodies, DNA, aptamers, molecularly imprinted polymers, microorganisms and whole cells while the transducers can be chemical, electrochemical, optical, conductometric, impedimetric or piezoelectric. The performance of the BEAM nanoparticles was tested in a direct-charge transfer biosensor. The direct-charge transfer biosensor architecture is a modified design of the biosensor previously developed (Muhammad-Tahir Z; Alocilja E C (2003a), A conductometric biosensor for biosecurity. Biosensors and Bioelectronics 18, 1690-1695); and (Muhammad-Tahir Z; Alocilja E C (2003b), Fabrication of a disposable biosensor for *Escherechia coli* O157:H7 detection. IEEE Sensor Journal, 3(4), 345-351). The current biosensor is comprised of three membrane regions: the application region, the capture region, and the absorption region.

Biosensor fabrication and assembly. The application and the absorption pads were washed with distilled water three times to remove dirt and surface residues. The membranes were then air-dried and stored in a clean area before being used in the biosensor. For the capture membrane pad, the nitrocellulose membrane was first cleaned with distilled water followed by 10% (v/v) methanol for 45 minutes and air-dried. The membrane surface was treated with 0.5% glutaraldehyde for 1 h followed by target specific antibody attachment for 1 h using a reagent dispensing module Matrix 1600 (Kinematics Automation Inc. CA, USA). The application, capture and the absorption pads were assembled. After assembly of the membrane pads, the biosensors were cut into 5 mm strips using the programmable shear module Matrix 2360 (Kinematics Automation Inc. CA, USA). Silver electrodes were fabricated on the capture membrane surface at 0.5 mm distances apart. The biosensor strips were stored at 4° C. before use.

Biosensor testing and data analysis. One hundred microliters of nano BEAM particles were used to capture specific targets from a solution and applied to the application region of the biosensor. The sample was allowed to flow through the biosensor and the change in current flow with time across the silver electrodes in the biosensor was measured chrono amperometrically against a fixed potential of 50 mV using a potentiostat (Model 263A, Princeton Applied Research). The current change was also monitored in terms of resistance by a portable multimeter (BK precision) with RS-232 interface connected to a computer. The current change was monitored for 6 min at 2 min intervals. The biosensor testing was performed with varying concentrations of the selected target. A minimum of three replicates was performed for each experiment. A control test without the specific targets was performed for each set of testing. A concentration-response curve was developed. Statistical analysis of the data was carried out to differentiate the control from the different cell concentrations using the statistical analytical software ANOVA.

The nano BEAM materials and their applications are in the intermediate stages of development. The nano EAM materials have already been synthesized with varying iron oxide and polymer content and also been characterized based on their magnetic properties, electrical properties, nano scale dimensions, and composition. Biologically enhanced electrically-active magnetic (BEAM) nanoparticle development has been successfully carried out with antibodies and work has also been initiated with other biological materials like DNA and aptamers. The nano BEAM particles have been tested as a concentrator of targets by using model microorganisms such as *Bacillus cereus* and *Bacillus anthracis*. The competency of the nano BEAM materials as a separator and concentrator of targets has been estimated in both pure target solutions and complex matrices and confirmed by standard identification techniques. The biosensor applications of the nano BEAM materials have also been tested by evaluating the performance of the nanomaterials in a direct-charge transfer biosensor for detection of *Bacillus cereus* and *Bacillus anthracis* in pure samples of the targets and also in complex matrices.

This Example focused on the development of a nanomagnetic polymer based biosensor for the rapid detection of antigens in samples. Polyaniline nanoparticles having magnetic properties are first synthesized. The nanomagnetic polyaniline is then conjugated with target-specific antibodies and is used for the concentration of the target antigens from a liquid sample by applying a magnetic field. The nanomagnetic polyaniline-antibody-antigen complex formed is applied to the biosensor which is functionalized with set of secondary antibodies to the target antigen. The principle of antigen-antibody binding and electron charge flow through the polyaniline nanomagnets generates an electronic signal. Aqueous sample containing the polyaniline-antibody-antigen complex is transported from the application pad to the capture pad by capillary flow. Detection from sample application to final results is completed in 6 min. Current research is based on the optimization of various parameters influencing the biosensor.

The present invention particularly relates to biosensors and devices for rapid pathogen detection. The present invention provides a new class of biosensor devices particularly for the detection of pathogens such as *Escherichia coli* O157:H7 and *Bacillus anthracis*. The conductimetric biosensor device is preferably based on ferromagnetic particles bound to a conductive polymer bound to an antibody to provide antibody-antigen binding and has the sensitivity to detect as low as $1^{00}$ to $1^{01}$ cfu/mL of *E. coli* or *Bacillus anthracis* in 2 to 10 minutes. Detection is thus rapid, and can be automated, and computerized. Furthermore, by utilizing different antibodies the biosensor device can be adapted for the detection of different types of pathogens at the same time. The biosensor device can thus detect other disease-causing causing bacteria, toxins, pathogens, chemicals and potential biowarfare agents such as *Salmonella* and *Listeria monocytogenes*. The present invention can be particularly used to detect pathogens, proteins, and other biological materials of interest in food, water, and environmental samples. The biosensor device can also be used for onsite diagnostics and against potential bioterrorism. Users include food processing plants, meat packing facilities, fruit and vegetable packers, restaurants, food and water safety inspectors, food wholesalers and retailers, farms, homes, medical profession, import border crossing, the police force, military, space habitation and national security.

Particular markets for the biosensor device are, for instance, the corporate laboratories of various food processing plants and environmental agencies. Rapid, simple, and accurate on-site testing provides considerable value to food producers by ensuring high product quality, greater yields, elimination of product recalls, and reduced treatment costs. The user friendly, biological analysis system results in more effective management of food processing lines and inventories, as well as safer food and water supplies. With the biosensor device of the present invention, the consumer does not have to make a choice between speed and sensitivity.

The present invention has two principal embodiments, a first with the single unit of the biosensor and second, with the multi-array system. The preferred objective of the invention is to provide a multi-array membrane strip biosensor using ferromagnetic particles bound to a conductive polymer, such as polyaniline as a reporter of a biological event using conductivity.

The present invention provides:
1. A biosensor that can detect an antigen at near realtime with an electronic data collection system.
2. A ferromagnetic particle conductive polymer-labeled antibody as reporter of biological event, such as antibody-antigen interaction.
3. Membrane strips in the construction of a sample application pad or membrane, optional capture pad and signal generation pad or membrane, and absorption pad or membrane that allow for the efficient transport of the sample by capillary action.
4. A multi-array system of the biosensor for multiple and simultaneous detection of different analytes (antigens, toxins, and the like) in the sample matrix.

The advantages of the present invention over previous approaches are shown in Table 1:

TABLE 1

| Parameters | Present Invention | Previous Methods |
|---|---|---|
| Number of bacterial species detected per test | Multiple | Single |
| Sensitivity | $10^0$-$10^1$ cfu[1] | $10^6$ or $10^7$ cfu/ml |
| Detection time after sample application | 2-10 minutes | 30-60 min or 24-48 hr |
| Size | 5 × 40 × 1 mm³ (strip only) 25 × 75 × 2 mm³ (total) | bulky |
| Portability | Field-based | laboratory-based |
| Signal measurement | Electronic | Manual or electronic |
| Use of reagents | None | Many |
| Use of colloidal gold | None | Sometimes |

TABLE 1-continued

| Parameters | Present Invention | Previous Methods |
|---|---|---|
| Skill requirement to operate | Minimal | Training and skills required |

[1]cfu—Colony forming units

It is intended that the foregoing description be only illustrative of the present invention and that the present invention be limited only by the hereinafter appended claims.

REFERENCE

1. Pal, S., Alocilja, E. C., Downes, F. P., *Biosensors & Bioelectronics,* 2007, 22, 2329-2336.

We claim:

1. A test kit which comprises:
    (a) a biosensor device for detecting an analyte, the biosensor device comprising a strip of a substrate having at least two zones, wherein:
        (1) a first of the zones comprises (A) a first capture reagent for the analyte bound to or as a moiety of the substrate in a defined area and (B) spaced apart electrodes defining sides of the defined area for providing an electrical bias to the defined area; and
        (2) a second of the zones comprises a fluid transfer medium for supplying a fluid to the first zone; and
    (b) a nanoparticle composition which is ferromagnetic particles bound to a conductive polymer bound to a second capture reagent for the analyte, wherein the weight ratio of conductive polymer to ferromagnetic particles in the nanoparticle composition ranges from 0.6 to 0.8;
    wherein when a fluid sample comprising a complex comprising the analyte bound to the second capture reagent of the nanoparticle composition is provided in the second of the zones, the complex migrates to the first zone in the fluid transfer medium and the analyte is bound by the first capture reagent thereby altering a conductivity or resistance of the defined area in the first zone as measured between the electrodes to detect the analyte.

2. The test kit of claim 1 wherein the nanoparticle composition which is the ferromagnetic particles bound to the conductive polymer bound to the second capture reagent is provided in a separate container in the test kit.

3. The test kit of claim 1 wherein the nanoparticle composition which is the ferromagnetic particles bound to the conductive polymer bound to the second capture reagent is placed in the second zone of the biosensor device so that the analyte can bind to the composition in the second zone to form the complex.

4. The test kit of claim 1 wherein the device further comprises a third zone adjacent to the first zone into which the fluid is absorbed after passing through the defined area of the first zone.

5. The test kit of any one of claim 1 or 2 wherein the defined area has a dimension between the electrodes of 1.0 mm or less.

6. The kit of claim 1 wherein one or both of the capture reagents are antibodies.

7. The test kit of claim 1 wherein the biosensor device further comprises a pad adjacent to the second zone for applying the fluid sample comprising the analyte prior to being introduced into the second zone.

8. The test kit of claim 1 wherein the biosensor device is a multi-array device comprising: a plurality of first zones on the single strip of substrate, each of the first zones having a first capture reagent with a different specificity bound to the single strip of substrate between electrodes to immobilize one of multiple analytes on the single strip of substrate so that each of the multiple analytes can be detected from the same sample on the single strip of substrate of the multi-array biosensor device.

9. The test kit of claim 1 further comprising a magnet for separation of the complex of the ferromagnetic particles bound to the conductive polymer bound to the second capture reagent bound to the analyte from a starting fluid sample.

10. The test kit of claim 1, wherein the nanoparticle composition has an average diameter ranging from 50 nm to 200 nm.

11. The test kit of claim 1, wherein the nanoparticle composition has an average diameter ranging from 50 nm to 90 nm.

12. A method for detecting an analyte in a fluid sample, the method comprising:
(a) providing a biosensor device for detecting the analyte, the biosensor device comprising a strip of a substrate having at least two zones, wherein:
(1) a first of the zones comprises (A) a first capture reagent for the analyte bound to or as a moiety of the substrate in a defined area and (B) spaced apart electrodes defining sides of the defined area for providing an electrical bias to the defined area; and
(2) a second of the zones comprises a fluid transfer medium for supplying a fluid to the first zone;
(b) providing a fluid sample comprising a complex comprising (1) the analyte and (2) a nanoparticle composition which is ferromagnetic particles bound to a conductive polymer bound to a second capture reagent for the analyte, wherein the weight ratio of conductive polymer to ferromagnetic particles in the nanoparticle composition ranges from 0.6 to 0.8, and the analyte is bound to the second capture reagent of the nanoparticle composition in the complex;
(c) providing the fluid sample comprising the complex in the second zone in the fluid transfer medium and allowing the complex to migrate to the first zone in the fluid transfer medium where the analyte is bound by the first capture reagent thereby altering a conductivity or resistance of the defined area in the first zone as measured between the electrodes; and
(d) measuring how the conductivity, resistance or magnetic property of the defined area is altered due to the presence of the conductive polymer bound to the ferromagnetic particles to detect the analyte.

13. The method of claim 12 wherein the nanoparticle composition which is the ferromagnetic particles bound to the conductive polymer bound to the second capture reagent is provided in a container in a test kit.

14. The method of claim 12 wherein the nanoparticle composition which is ferromagnetic particles bound to the conductive polymer bound to the second capture reagent is placed in the second zone of the biosensor device so that the analyte can bind to the composition in the second zone to form the complex.

15. The method of claim 12 wherein the device further comprises a third zone adjacent to the first zone into which the fluid is absorbed after passing through the defined area of the first zone.

16. The method of claim 12 wherein the defined area has a dimension between the electrodes of 1.0 mm or less.

17. The method of claim 12 wherein one or both of the capture reagents are antibodies.

18. The method of claim 12 wherein the biosensor device further comprises a pad adjacent to the second zone to which the fluid sample comprising the analyte is applied prior to being introduced into the second zone.

19. The method of claim 12 wherein the biosensor device is a multi-array device comprising: a plurality of first zones on the single strip of substrate, each of the first zones having a first capture reagent with a different specificity bound to the single strip of substrate between electrodes to immobilize one of multiple analytes on the single strip of substrate so that each of the multiple analytes are detected from the same sample on the single strip of substrate of the multi-array biosensor device.

20. The method of claim 12 wherein the analyte bound to the second capture reagent is magnetically separated from a starting fluid sample before being provided in the second zone of the device.

21. The method of claim 12, wherein the nanoparticle composition has an average diameter ranging from 50 nm to 200 nm.

22. The method of claim 12, wherein the nanoparticle composition has an average diameter ranging from 50 nm to 90 nm.

23. A system for detecting an analyte in a fluid sample, the system comprising:
(a) a biosensor device for detecting the analyte, the biosensor device comprising a strip of a substrate having at least two zones, wherein:
(1) a first of the zones comprises (A) a first capture reagent for the analyte bound to or as a moiety of the substrate in a defined area and (B) spaced apart electrodes defining sides of the defined area for providing an electrical bias to the defined area; and
(2) a second of the zones comprises a fluid transfer medium for supplying a fluid to the first zone; and
(b) a nanoparticle composition which is ferromagnetic particles bound to a conductive polymer bound to a second capture reagent for the analyte; wherein the weight ratio of conductive polymer to ferromagnetic particles in the nanoparticle composition ranges from 0.6 to 0.8, and when a fluid sample comprising a complex comprising the analyte bound to the second capture reagent of the nanoparticle composition is provided in the second zone, the complex migrates to the first zone in the fluid transfer medium and the analyte is bound by the first capture reagent thereby altering a conductivity or resistance of the defined area in the first zone as measured between the electrodes;
(c) an electrical means for supplying an electrical bias between the electrodes; and
(d) a measuring means for determining a change in the conductivity or resistance of the defined area before and after the complex is bound in the first zone.

24. The system of claim 23 wherein one or both of the capture reagents are antibodies.

25. The system of claim 23 wherein the biosensor device further comprises a pad adjacent to the second zone for applying the fluid sample comprising the analyte prior to being introduced into the second zone.

26. The system of claim 23 wherein the biosensor device is a multi-array device comprising: a plurality of first zones on the single strip of substrate, each of the first zones having a first capture reagent with a different specificity bound to the single strip of substrate between electrodes to immobilize one of multiple analytes on the single strip of substrate so that each of the multiple analytes can be detected from the sample on the single strip of substrate of the multi-array biosensor device by providing a constant current and measuring generated voltage signals proportional to resistances across each of the first zones.

27. The system of claim 23 further comprising a magnet for separation of the complex of the ferromagnetic particles bound to the conductive polymer bound to the second capture reagent bound to the analyte from a starting fluid sample.

* * * * *